United States Patent
Norwood et al.

(10) Patent No.: US 9,645,045 B2
(45) Date of Patent: May 9, 2017

(54) SHG IMAGING TECHNIQUE FOR ASSESSING HYBRID EO POLYMER/SILICON PHOTONIC INTEGRATED CIRCUITS

(71) Applicant: The Arizona Board of Regents on Behalf of the University of Arizona, Tucson, AZ (US)

(72) Inventors: Robert A. Norwood, Tucson, AZ (US); Khanh Q. Kieu, Tucson, AZ (US); Roland Himmelhuber, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/437,776

(22) PCT Filed: Oct. 22, 2013

(86) PCT No.: PCT/US2013/066176
§ 371 (c)(1),
(2) Date: Apr. 22, 2015

(87) PCT Pub. No.: WO2014/066384
PCT Pub. Date: May 1, 2014

(65) Prior Publication Data
US 2015/0292981 A1  Oct. 15, 2015

Related U.S. Application Data

(60) Provisional application No. 61/795,651, filed on Oct. 22, 2012.

(51) Int. Cl.
*G01N 21/00* (2006.01)
*G01M 11/00* (2006.01)
(Continued)

(52) U.S. Cl.
CPC ........... *G01M 11/37* (2013.01); *G01N 21/636* (2013.01); *G02B 21/002* (2013.01);
(Continued)

(58) Field of Classification Search
CPC ........... G01M 11/3145; G01M 11/335; G01M 11/33; G01M 11/3109; G01M 11/338
(Continued)

(56) References Cited

U.S. PATENT DOCUMENTS

| | | | |
|---|---|---|---|
| 5,276,743 A | 1/1994 | Penner et al. | |
| 5,322,986 A | 6/1994 | Nutt | |

(Continued)

OTHER PUBLICATIONS

Baehr-Jones et al., "Polymer silicon hybrid systems: a platform for practical nonlinear optics," *J. Phys. Chem. C* 112:8085-8090 (Apr. 2008).

(Continued)

*Primary Examiner* — Tarifur Chowdhury
*Assistant Examiner* — Md M Rahman
(74) *Attorney, Agent, or Firm* — Klarquist Sparkman, LLP

(57) ABSTRACT

Probe beams are scanned with respect to waveguide substrates to generate optical harmonics. Detection of the optical harmonic radiation is used to image waveguide cores, claddings, or other structures such as electrodes. The detected optical radiation can also be used to provide estimates of linear electrooptic coefficients, or ratios of linear electrooptic coefficients. In some cases, the poling of polymer waveguide structures is monitored during fabrication based on a second harmonic of the probe beam. In some examples, third harmonic generation is used for imaging of conductive layers.

18 Claims, 6 Drawing Sheets

(51) Int. Cl.
*G01N 21/63* (2006.01)
*G02B 21/00* (2006.01)
*G01N 21/23* (2006.01)
*G01N 21/21* (2006.01)
*G01N 21/65* (2006.01)

(52) U.S. Cl.
CPC ......... *G02B 21/0016* (2013.01); *G01N 21/23* (2013.01); *G01N 2021/218* (2013.01); *G01N 2021/637* (2013.01); *G01N 2021/653* (2013.01)

(58) Field of Classification Search
USPC .......................................................... 356/73.1
See application file for complete search history.

(56) References Cited

U.S. PATENT DOCUMENTS

| | | | |
|---|---|---|---|
| 5,828,459 A | 10/1998 | Silberberg | |
| 8,380,016 B1 | 2/2013 | Hochberg et al. | |
| 2002/0094528 A1 | 7/2002 | Salafsky | |
| 2003/0086672 A1* | 5/2003 | Takayama | G02B 6/1221 385/129 |
| 2005/0139813 A1* | 6/2005 | Yamaguchi | G02F 1/3611 252/582 |
| 2008/0100834 A1 | 5/2008 | Kung et al. | |
| 2008/0111735 A1* | 5/2008 | Ridgway | G01S 7/03 342/200 |
| 2008/0151349 A1* | 6/2008 | Hochberg | H01S 1/02 359/258 |
| 2009/0323059 A1 | 12/2009 | Sun et al. | |

OTHER PUBLICATIONS

Beerman et al., "High-resolution second-harmonic microscopy of poled silica waveguides," *Opt. Comm.* 221:295-300 (Jun. 2003).
Ding et al., "Demonstration of a low VπL modulator with GHz bandwidth based on electro-optic polymer-clad silicon slot waveguides," *Optics Express* 18:15618-15623 (Jul. 2010).
Gadret et al., "Nonlinear Optical Properties of Poled Polymers," *Proceedings of SPIE*, 1560: 226-237 (Jul. 1991).
Himmelhuber et al., "Characterization of coplanar poled electro optic polymer films for Si-photonic devices with multiphoton microscopy," 2013 Optical Interconnects Conference, pp. 90-91 (May 2013).
International Search Report and Written Opinion from International Application No. PCT/US2013/066176, dated Dec. 11, 2013, 15 pages.
Nahata et al., "Electrooptic characterization of organic media," *IEEE Trans. Inst. Meas.* 41:128-131 (Feb. 1992).
Oh et al., "Integrated-optic polarization controlling devices using electro-optic polymers," *ETRI Journal* 18:287-299 (Jan. 1997).
Park, "Characterization of linear electro-optic effect of poled organic thin films," University of Maryland, 204 pages, (Feb. 2008).
Tang et al., "Novel poling and electro-optic measurement methods of cladded nonlinear-optical polymer films," SPIE vol. 3147, pp. 156-164 (Oct. 1997).
Toury et al., "Electro-optical microscopy: mapping nonlinear polymer films with micrometric resolution," *Optics Letters*, 31:1468-1470 (May 2006).

* cited by examiner

SHG IMAGING TECHNIQUE FOR ASSESSING HYBRID EO POLYMER/SILICON PHOTONIC INTEGRATED CIRCUITS

CROSS REFERENCE TO RELATED APPLICATIONS

This is the U.S. National Stage of International Application No. PCT/US2013/066176, filed Oct. 22, 2013, which was published in English under PCT Article 21(2), and claims the benefit of U.S. Provisional Application No. 61/795,651, filed Oct. 22, 2012, which is herein incorporated by reference in its entirety.

ACKNOWLEDGMENT OF GOVERNMENT SUPPORT

This invention was made with government support under Grant No. EEC0812072 awarded by the National Science Foundation. The government has certain rights in the invention.

FIELD

The disclosure pertains to evaluation of waveguide devices.

BACKGROUND

Polymer based electrooptic devices can be used to provide high speed modulation of optical signals at relatively low voltages. While polymers as deposited generally do not exhibit the linear electrooptic effect, application of suitable electric fields at suitable temperatures establishes polymer configurations that exhibit the electrooptic effect, typically as associated with symmetry group mm∞ so as to have nonzero electrooptic coefficients $r_{33}$ and $r_{13}$. Polymers can be poled in this way so that electrooptic coefficients on the order of 100 pm/V are produced. Polymers can be deposited on a variety of substrates, including semiconducting substrates such as silicon so that optical waveguide devices and electronic devices can be integrated on a common substrate.

One drawback of polymer based waveguide devices is the necessity of inducing the electrooptic effect in a polymer layer. This "poling" process must generally be performed on an otherwise virtually completed device. Thus, for example, defective polymer layers may not be identified until the end of processing, so that process steps are wasted. In addition, while devices are subject to suitable poling conditions during fabrication, the extent of poling throughout such devices cannot be determined until poling is completed. Additional approaches to evaluating and fabricating waveguide devices that include electrooptic polymer layers are needed.

SUMMARY

Methods and apparatus are disclosed that permit imaging and assessment of waveguide devices, including poled polymer devices, prior to, during, and after fabrication. Detection of nonlinear optical radiation responsive to a focused laser beam at a fundamental wavelength is used to estimate a linear electrooptic coefficient, or to determine if a particular device is satisfactory in comparison with a reference device whose nonlinear radiation production has been previously established.

In some examples, apparatus comprise a substrate stage configured to retain a waveguide defined by a polymer layer on a substrate. A beam scanner is configured to scan a focused optical beam in a direction parallel to an axis of the waveguide, wherein the focused optical beam is at a fundamental wavelength. An optical detection system is configured to detect nonlinear optical radiation from the waveguide responsive to the focused optical beam. A processing system produces an image of at least a portion of the waveguide based on the scanning of the focused optical beam and the detected optical radiation. Typically, the detected nonlinear optical radiation is at a wavelength corresponding to a harmonic of the focused optical beam, and the polymer layer is a waveguide cladding layer or a waveguide core layer. In some examples, the detected nonlinear optical radiation is a third harmonic of the focused optical beam and is associated with waveguide device conductor layers needed for voltage application. The detected nonlinear optical radiation can be monitored during a poling process applied to the polymer layer so as to estimate a poling extent in the polymer layer. In some cases, electrooptic coefficient values corresponding to values of $r_{33}$ or $r_{13}$ or a ratio thereof are produced.

Representative methods comprise directing a focused optical beam to a waveguide device and scanning the focused optical beam in a direction parallel to an axis of propagation in the waveguide device. Nonlinear optical radiation responsive to the focused optical beam and the waveguide device is detected. In some examples, an estimate of an electrooptic coefficient or a ratio of electrooptic coefficients is obtained based on the detected nonlinear optical radiation. In some examples, the detected nonlinear optical radiation is obtained with the waveguide device exposed to polymer poling conditions, and used to adjust poling conditions or to indicate that poling can be discontinued. In typical examples, the detected nonlinear optical radiation is second or third harmonic optical radiation.

In other examples, waveguide device processing apparatus comprise a pulsed laser configured to provide a series of optical pulses at a fundamental wavelength and a scanning system configured to scan the optical pulses. A voltage source is situated to establish a poling electric field in at least a portion of a polable polymer layer and a temperature controller is situated to establish a selected temperature in the portion of the polable polymer layer. A detection system detects nonlinear optical radiation produced in response to the optical pulses. A processing system is coupled to the detection system and configured to control the poling electric field and the selected temperature based on the detected nonlinear optical radiation, and produce an image of the portion of the polymer layer and an estimate of an electrooptic coefficient.

The foregoing and other objects, features, and advantages of the disclosed technology will become more apparent from the following detailed description, which proceeds with reference to the accompanying figures.

BRIEF DESCRIPTION OF THE DRAWINGS

FIG. 3A is a combined second and third harmonic image. FIGS. 3B and 3C are second and third harmonic images, respectively.

DETAILED DESCRIPTION

Figure 1A:
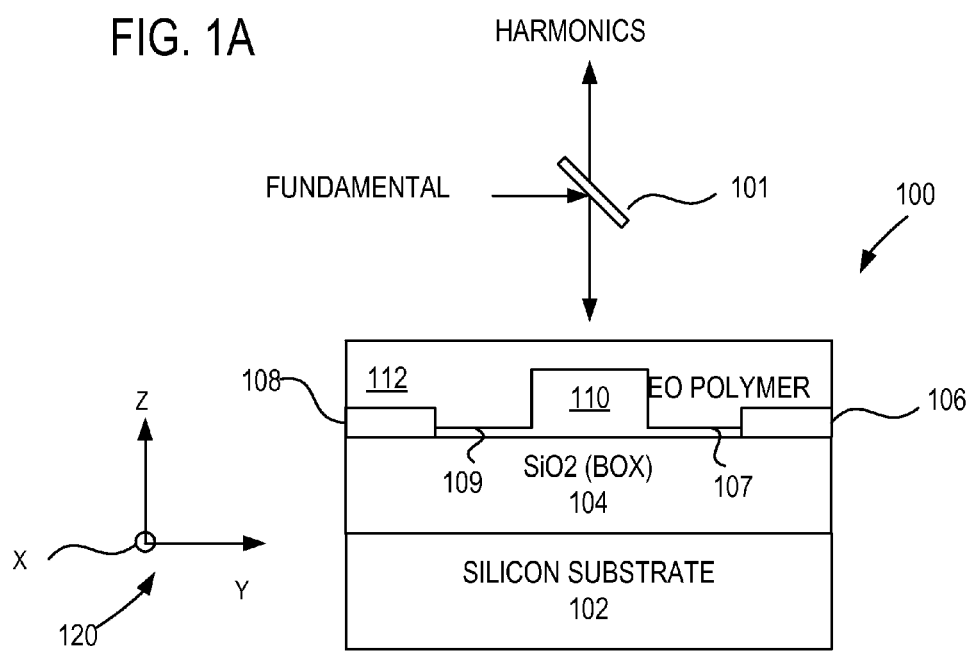
FIG. 1A illustrates a representative silicon waveguide having an electrooptic polymer cladding and exposed to a focused optical beam at a fundamental wavelength so as to produce optical harmonics, and separate the fundamental wavelength from the harmonics.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

As used herein, the term "image" refers to a visual image that is presented for viewing on a display device or otherwise made available for viewing. In addition, the term "image" also refers to acquired or recorded data that associate a magnitude value such an optical power, optical intensity, an electrooptic coefficient, or a nonlinear coefficient or intensity with a spatial location. For example, such an image can include optical power value in a two dimensional array of spatial locations. Such data-based images can be arranged in other ways as well, and can be used to form viewable images.

In some examples, properties of polymer layers or other layers or features that define an optical waveguide are disclosed. For convenient description, a waveguide axis refers to propagation axis of optical radiation guided by the waveguide. In some examples, a waveguide axis is a linear axis or comprises two or more linear sections, but a waveguide axis can be bent or curved depending on how waveguide core and claddings are arranged, and is not restricted to one or more line segments.

In some examples, optical radiation in a first wavelength range is directed to a sample and is subject to one or more nonlinear optical processes at the sample such as second, third, or higher harmonic generation, sum and frequency generation, stimulated Brillouin or Raman scattering, coherent anti-Stokes Raman scattering (CARS) or other processes that produce optical radiation in a second wavelength range that is different than the first wavelength range. Optical radiation in the first wavelength range is referred to herein as being at a fundamental wavelength. In some cases, the second wavelength range is associated with second harmonic generation (SHG), third harmonic generation (THG) or other nonlinear conversion processes. In other examples, optical radiation at first and second (or more) wavelengths are directed to a sample to produce optical radiation at a third wavelength corresponding to a sum frequency, a difference frequency, or a frequency associated a sum or difference frequency associated with a molecular vibrational frequency (such as in CARS). In some examples, nonlinear radiation is associated with induced polarization that are functions of powers of an applied input field, i.e., polarizations of the form $P(t)=\chi^{(2)}E^2(t)+\chi^{(3)}E^3(t)+\ldots$. In many cases, terms involving $\chi^{(2)}$ and $\chi^{(3)}$ are associated with nonlinear radiation that is selected for device characterization. As used herein, optical radiation used for specimen analysis and imaging is obtained via a nonlinear process based on one or more incident optical beams directed to the specimen and such optical radiation is in a second wavelength range different from a first wavelength range associated with the incident beam. For convenience, optical radiation in such a second wavelength range can be referred to as a nonlinear optical power.

In some disclosed examples, nonlinear optical power is generated in materials having suitable symmetry properties that also exhibit an electrooptic effect, such as poled polymers or crystalline materials. However, nonlinear optical power can also be generated in a variety of materials as well by, for example, third harmonic generation in silicon or CARS in suitable materials. In materials exhibiting electrooptic effect, nonlinear coefficients associated with harmonic generation are related to corresponding electrooptic coefficients, and measurement of one can be indicative of a value of the other. Electrooptic coefficients are generally referred to as r values herein, and nonlinear coefficients are referred to as d values.

In some examples, optical beams are scanned with respect to a specimen so as to acquire one or more specimen images. For convenience, beams are referred to as being scanned in a direction parallel to an axis when a beam scan path has a component of displacement along the axis. Such scanning need not be exclusively along the axis. For example, in an xyz-coordinate system, scanning a beam so as to trace a path in an xy-plane results in scanning along both the x-axis and the y-axis. While a beam can be conveniently scanned in a raster pattern, a beam can be scanned in other configurations to obtain specimen measurements. In the disclosed examples, an optical beam is scanned with an optical scanning device, but optical beams can be effectively scanned based on one or both of beam scanning and substrate translation.

As used herein, optical radiation refers to electromagnetic radiation in a wavelength range of 100 nm to 10 μm, but in many examples, wavelengths between about 250 nm and 2 μm, or 400 nm and 1.6 μm are used.

Process and instrument controllers can be based on stand-alone or networked computers, and operating instructions for the disclosed methods stored on one or more computer readable storage devices such as RAM, ROM, hard disks, solid state disk drives, or other storage devices. Data obtained with the disclosed methods and devices can be similarly stored.

Example 1

Representative Waveguide Configurations

A representative configuration for SHG based assessment of a waveguide 100 is illustrated in FIG. 1A. An incident optical beam at a fundamental wavelength is directed to a dichroic beam-splitter 101 that reflects the fundamental beam to a silicon ridge 110 that is partially covered with an electrooptic poled polymer 112. Metallic electrodes 106, 108 are electrically coupled to silicon layer contacts 107, 109 respectively, so as to establish an electric field in a region around the silicon ridge. In the example of FIG. 1A, the polymer layer 112 is arranged as a cladding layer and the silicon ridge 110 as a core layer. A propagation axis in the silicon ridge is parallel to a x-axis of a coordinate system 120. Harmonic optical power generated in response to the incident optical beam is received by the beam-splitter 101. Harmonic power can be received directly as generated in the polymer or other layers, and as reflected from a silicon/SiO$_x$ or other interface. Poling of the polymer layer 112 can be performed by applying a suitable voltage to the electrodes 106, 108 or a poling field can be otherwise provided, and SHG power can be used to assess poling extent.

Figure 1B:
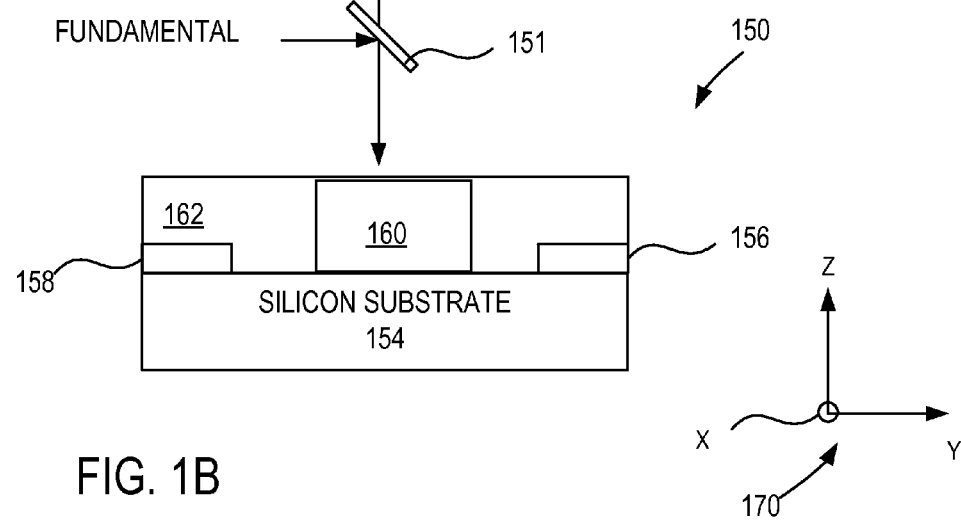
FIG. 1B illustrates a representative waveguide having a poled polymer core and exposed to an optical beam at a fundamental wavelength so as to produce optical harmonics of the fundamental wavelength.

A representative configuration for SHG based assessment of an alternative waveguide 150 is illustrated in FIG. 1B. An incident optical beam at a fundamental wavelength is directed to a dichroic beam-splitter 151 that reflects the fundamental beam to a core region 160 of poled polymer layer 162. Gold or other metallic electrodes 156, 158 situated on a silicon substrate 154 are electrically coupled to establish an electric field in the core region 160. A propagation axis in the core region 160 is parallel to a x-axis of a coordinate system 170. Harmonic optical power generated in response to the incident optical beam is received by the beam-splitter 151. Harmonic power can be received directly as generated in the polymer or other layers, and as reflected from a silicon/polymer or other interface. Poling of the polymer layer 162 can be performed by applying a suitable voltage to the electrodes 156, 158 or a poling field can be otherwise provided, and SHG power can be used to assess poling extent.

The examples of FIGS. 1A-1B are provided for illustration purposes, and waveguides made of silicon, silicon nitride, graphene or other materials can be used with the disclosed methods and apparatus. While non-centrosymmetric materials that exhibit a linear electrooptic effect are often used, centrosymmetric materials can be used in conjunction with suitable nonlinear processes such as CARS or third harmonic generation.

Example 2

Multiphoton Imaging Systems

Figure 2:
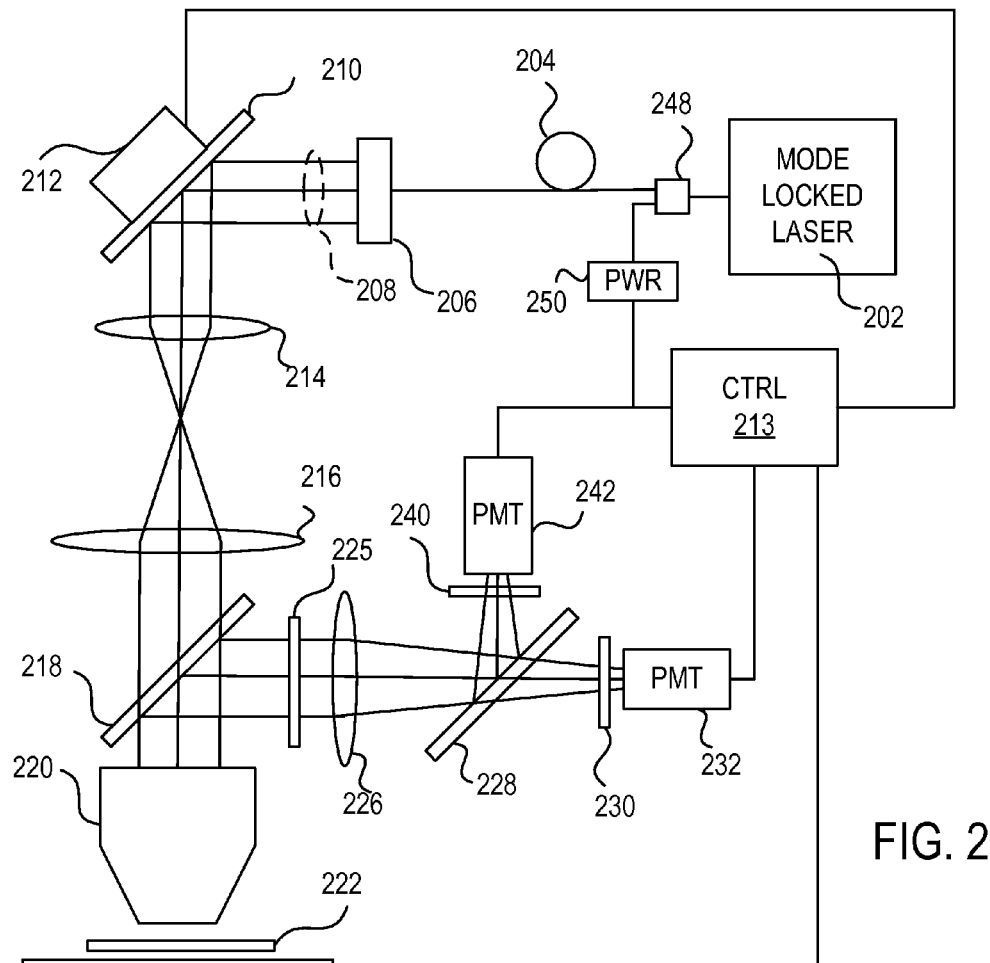
FIG. 2 is an imaging system that scans a pulsed laser beam at a fundamental frequency across a waveguide device under test and records power in second and third harmonic beams so as to produce second and third harmonic images.

Referring to FIG. 2, a representative multi-photon imaging system 200 includes an excitation optical source 202 that produces optical radiation at a fundamental frequency, or a combination of fundamental frequencies. For the generation of optical harmonics, optical sources that can produce high optical powers in short optical pulses are typically preferred. The excitation optical source is selected to produce optical radiation at a suitable wavelength (fundamental frequency) based on a device to be tested. Mode-locked lasers can be used. In one example, a mode-locked fiber laser that includes a carbon nanotube saturable absorber (CNT SA) is used that produces femtosecond (fs) optical pulses at about 1560 nm. This wavelength is within a so-called 1500 nm telecommunications window.

The optical beam from the source 202 is coupled via optical fiber 204 to a beam expander/collimator 206 that produces a substantially collimated fundamental beam 208. A beam scanner 212 includes a scan mirror 210 that is rotatable so as to scan the fundamental beam. In a representative example, the beam scanner 212 is a galvanometer scanner, but other types of scanners such as polygonal mirror scanners, electrooptic scanners, or other systems can be used. In a representative example, the input fs laser beam is raster-scanned on a sample 222 using a 2D galvanometer scanner system. The scan mirror 210 directs the beam to a scan lens 214 and a tube lens 216 arranged as a telescopic system that permits beam expansion to a selected beam diameter. The tube lens 216 directs the expanded (or contracted) beam to a dichroic beam-splitter 218 and to an objective lens 220. The dichroic beam-splitter 218 is selected to separate a fundamental wavelength from its optical harmonics. For example, for a 1560 nm fundamental wavelength, optical harmonics such as a second harmonic at 780 nm and a third harmonic at 520 nm are separated from the 1560 nm fundamental. As shown in FIG. 2, the fundamental wavelength is transmitted and the harmonics are reflected by the beam-splitter 218, but in other examples the fundamental is reflected and the harmonics are transmitted.

The objective lens 220 is situated to produce a focused beam that is directed to the sample 222 that is secured to an XYZ-translation stage 224. In other examples the beam delivery optical system and scanning systems can be translated with respect to the sample 222, but it is generally more convenient to secure the sample 222 to a translation stage. To increase resolution in images obtained by scanning a focused beam with respect to the sample 222, the expanded beam is configured to fully irradiate a back aperture of the objective lens 220 so as to use the full NA of the objective lens 220 and produce a small focused laser spot size on the sample 222.

The objective lens 220 is also situated to collect at least a portion of any harmonic radiation generated at the sample 222. The harmonic radiation is collected by the objective lens 220 and directed to the dichroic beam-splitter 218. A focusing lens 226 receives the harmonic radiation from the beam-splitter 218 and directs the harmonic radiation to a dichroic beam-splitter 228 that is selected to separate various optical harmonics. A filter 225 is situated to block the fundamental wavelength, and transmit the harmonics. For example, as shown in FIG. 2, the beam-splitter 228 transmits second harmonic radiation at 780 nm to a photodetector 232 through a bandpass filter 230. The photodetector 232 can be a silicon, germanium, or other photodiode or avalanche photodiode or other type of detector, but typically a photomultiplier tube (PMT) is used. The bandpass filter 230 rejects optical radiation at the fundamental wavelength and at other harmonics of the fundamental (and any other radiation that is out of a band associated with the second harmonic). The beam-splitter 228 similarly directs (by reflection) third harmonic radiation to a photodetector 242 through a bandpass filter 240. The photodetector 242 can be a silicon, germanium, or other photodiode or avalanche photodiode or other type of detector, but typically a photomultiplier tube (PMT) is used. The bandpass filter 240 rejects optical radiation at the fundamental wavelength and at other harmonics of the fundamental (and any other radiation that is out of a band associated with the third harmonic).

A data analysis and control system 213 is coupled to the scanner 212, the XYZ-stage 224, and the detectors 232, 242. Based on a beam scan angle and sample position as provided by the XYZ-stage 224, detected harmonic powers at one or more harmonics are recorded and associated with beam locations at the sample 222. The control system 213 can then process the recorded powers to produce two or three dimensional sample images at one or more harmonics either individually or in combination. Such images are based on optical nonlinearities associated with a harmonic such as second and third order nonlinearities. In addition, a power monitor detector 250 is coupled to the control system 213 and provides an indication of optical beam power received from a fiber coupler 248. In some examples, a variable attenuator is provided to confirm that harmonic power scales appropriately with fundamental power.

Figures 3A, 3B, 3C:
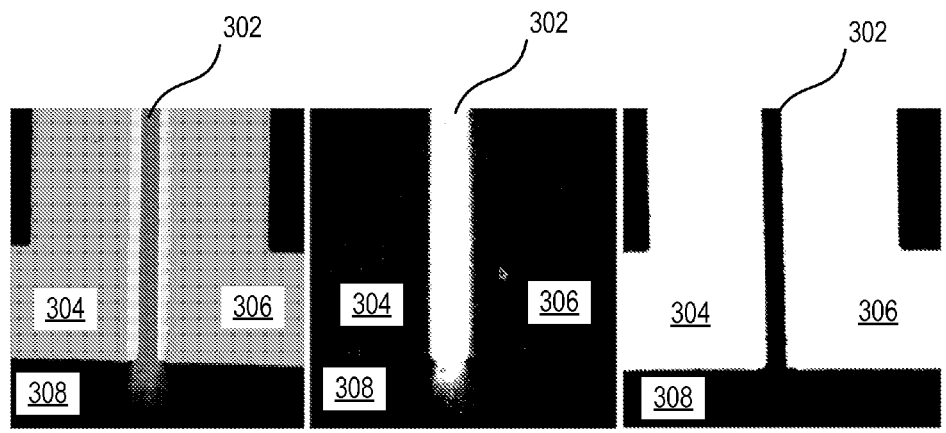
FIGS. 3A-3C are images of a representative waveguide device based on second and third harmonic generation.

FIGS. 3A-3C are images of a coplanar poled polymer film on $SiO_2$ on silicon. A poled polymer waveguide 302 is situated between gold electrodes 304, 306 on an $SiO_2$ surface provided on a silicon substrate. FIG. 3A is a composite image based on a combination of detected second and third harmonic radiation. FIG. 3B is an image based on second harmonic radiation alone, and FIG. 3C is an image based on third harmonic radiation alone. FIG. 3B shows that second harmonic generation occurs at the poled waveguide 302. FIG. 3C shows third harmonic generation at the gold electrodes 304, 306, likely enhanced by plasmonic effects. This enhancement is observable with both poled and unpoled waveguides.

Figure 4:
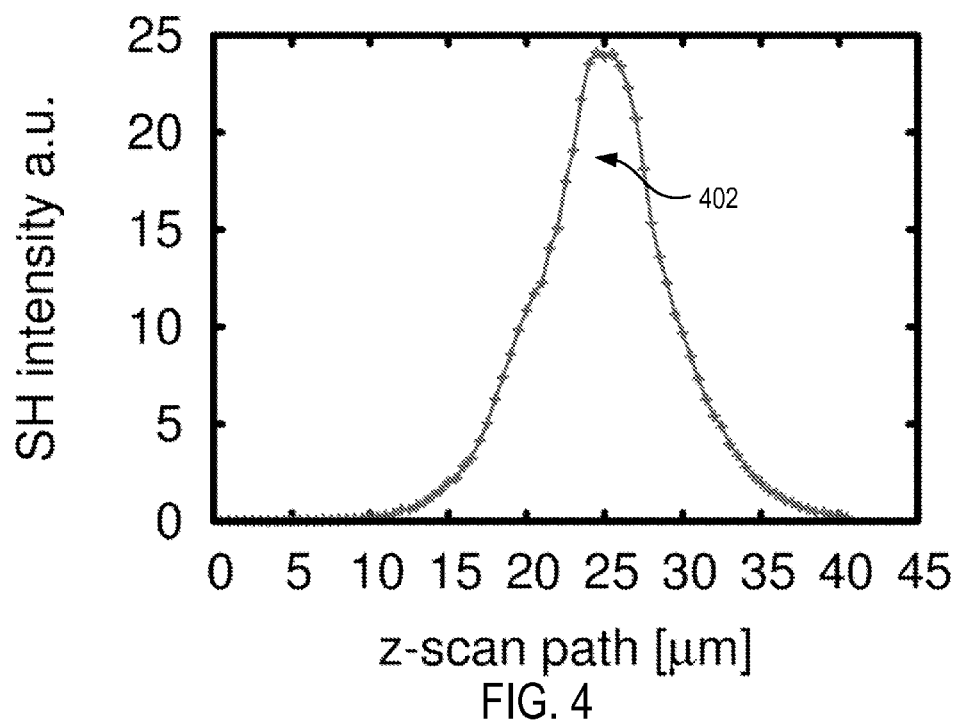
FIG. 4 illustrates second harmonic power generated as a function of a z-axis scan of a poled polymer layer.

FIG. 4 is a representative graph of measured second harmonic optical power as a function of z-coordinate in a z-scan of a particular polymer waveguide location. A z-scan can be obtained by translating the sample 222 in a z-direction with the stage 224, or with a z-adjustment of the objective 220. As shown in FIG. 4, a region 402 of maximum SHG power corresponds to z-displacements of about 2.5 μm, corresponding to waveguide thickness.

Figure 5:
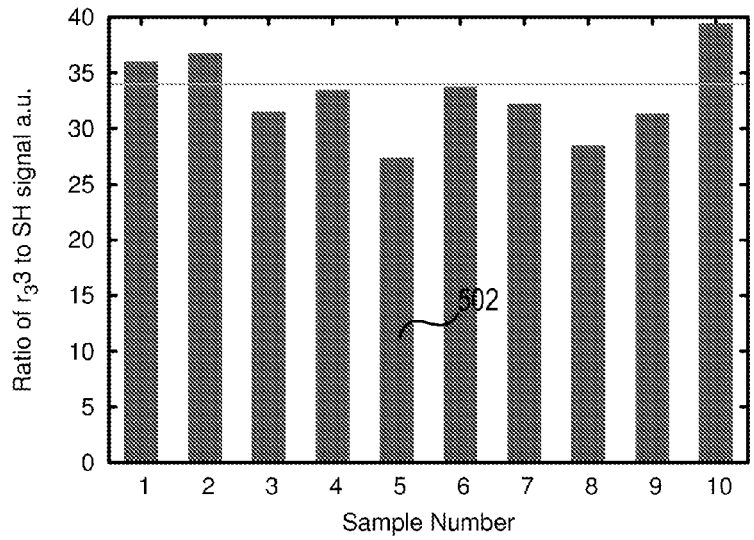
FIG. 5 illustrates a ratio of an electrooptic coefficient to second harmonic power for a number of poled polymer samples.

In many applications, a parameter of interest is an effective linear electrooptic (coefficient r (also known as a Pockels coefficient), and not a nonlinear d coefficient. SHG measurements (based on effective d coefficients) can be related to Pockels coefficients (r values) by comparing SHG powers for multiple samples. For example, SHG powers can be compared with $r_{33}$ measurements from the same samples. In one example, $r_{33}$ measurements were obtained with coplanar poled transparent samples irradiated at 1340 nm through a linear polarizer having an axis at 45° from a vertical poling direction. An electrical signal of RMS amplitude of 33.5 V at a frequency of about 1 kHz was applied to the electrodes. A phase difference between the p-component and s-component was obtained by measuring a change of intensity transmitted by a second linear polarizer at 45° from the poling direction. This phase change permits the electrooptic coefficient $r_{33}$ to be estimated. Details of this method are described by Nahata et. al., IEEE Trans. Instrum Meas., 41, 128, (1992). The second harmonic power depends quadratically on an effective d coefficient, and d coefficient magnitudes are generally related to linear electrooptic coefficients as described in Goodson et al., Macromolecules 27, 4278 (1994). For example, estimates of nonlinear coefficients FIG. 5 shows ratios of a measured $r_{33}$ value to a square root of second harmonic optical power for a variety of samples. A line 502 indicates an average value, and standard error of the mean was 0.54.

Estimates of $r_{33}$ can be obtained by applying a modulating field parallel to a poling direction in a poled polymer. Estimates of $r_{13}$ can be obtained in a similar fashion by applying a modulating field in direction perpendicular to the poling direction and a direction of propagation in corresponding waveguide core. Nonlinear coefficients $d_{33}$, $d_{13}$ can be similarly estimated based on input SOP of a fundamental.

For the data of FIG. 5, a transparent substrate was used. For waveguides on a silicon substrate, additional SHG power is collected due to reflection of SHG power at silicon/SiO2 interfaces, and additional SHG power generated by reflected fundamental power. For example, collected SHG power from a sample with a 1 μm thick oxide layer on top of silicon is about 30 times higher than that from a sample with only a poled polymer layer on $SiO_2$. With this correction factor, r values of poled polymers can be better estimated, and $r_{33}$ of a polymer film surrounding a silicon waveguide above a 1 μm thick oxide layer on silicon was estimated to be about 125 pm/V. A direct phase modulation based measurement provided a value of $r_{33}$ of about 132 pm/V, demonstrating that SHG-based characterization of poled polymer films can be used for estimate of r values and electrooptic waveguide evaluation.

Example 3

Waveguide Processing and Evaluation Systems

Figure 6:
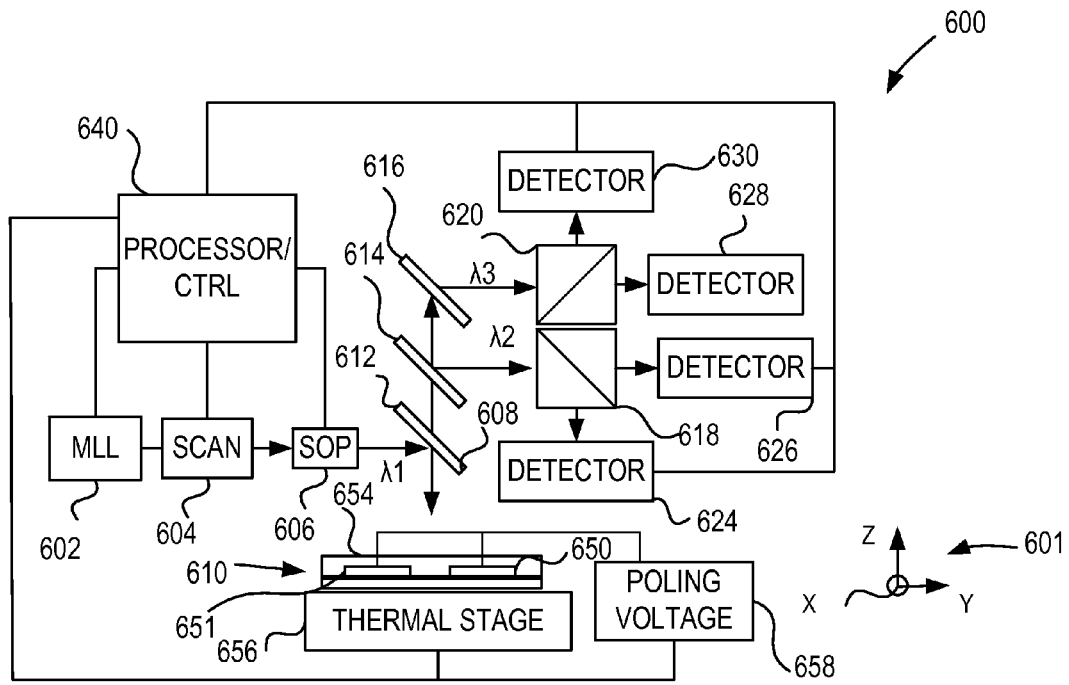
FIG. 6 is a block diagram of a waveguide processing apparatus configured to establish poling conditions in a polymer layer and evaluate poling extent based on nonlinear optical radiation.

With reference to FIG. 6, a waveguide evaluation system includes a mode locked laser 602 that directs a pulsed beam to a scanning system 604 and to a state of polarization (SOP) controller 606. A polarized, focused beam is scanned with respect to a waveguide substrate 610, typically along one or more of an x, y, or z-axis of a coordinate system 601. Nonlinear beams at different harmonic wavelengths and responsive to the focused beam are coupled by dichroic beam-splitters 612, 614 to respective polarizing beamsplitters (PBSs) 618, 620 that couple nonlinear radiation in different SOPs to detectors 624, 626 and 628, 630, respectively. A processor/controller 640 is coupled to the laser 602, the scanning system 604, the SOP controller 606, and the detectors 624, 626, 628, 630.

The waveguide substrate 610 includes a polymer layer 654 and electrodes 650, 651 situated on a substrate layer such as a silicon substrate. The waveguide substrate 610 is thermally coupled to a thermal stage 656, and the electrodes 650, 651 are coupled to a poling voltage source 658 so that suitable temperatures and electric fields can be established in the polymer layer 654 so as to produce a suitable electrooptic coefficient. Temperatures and voltages can be set as directed by the controller 640. In addition, an input SOP can be varied so that estimates of different electrooptic coefficients can be obtained. The focused beam from the laser 602 can be scanned for evaluation of the polymer layer or portions thereof, or to evaluate or image conductor layers. For example, gold conductors tend to produce third harmonic optical radiation that can be detected for device imaging and fabrication.

In typical examples, second and third harmonic optical beams are coupled to the polarizing beamsplitters 618, 620. Additional filters to improve rejection of unwanted wavelengths are not shown. Typically, the SOP controller 606 can be implemented as a half wave plate to produce selected linear SOPs, but other SOPs can be provided as desired. In the example of FIG. 6, a probe beam at a single wavelength is provided, but beams at more than one wavelength can be provided to produce nonlinear radiation based on sum or difference frequencies or other combinations of two or more beams. For example, a mode locked laser source can be configured to provide optical radiation at a fundamental wavelength and a harmonic thereof so as to produce higher harmonics in a specimen.

SOPs of nonlinear radiation typically depend on input (fundamental) beam SOPs and material properties. In some situations, analysis of nonlinear radiation can be enhanced based on an SOP associated with the nonlinear radiation. For example, SHG in poled polymers is produced in the same state of polarization as the fundamental, and orthogonally polarized radiation can be attenuated.

Example 4

Multiphoton-Based Device Fabrication

Figure 7:
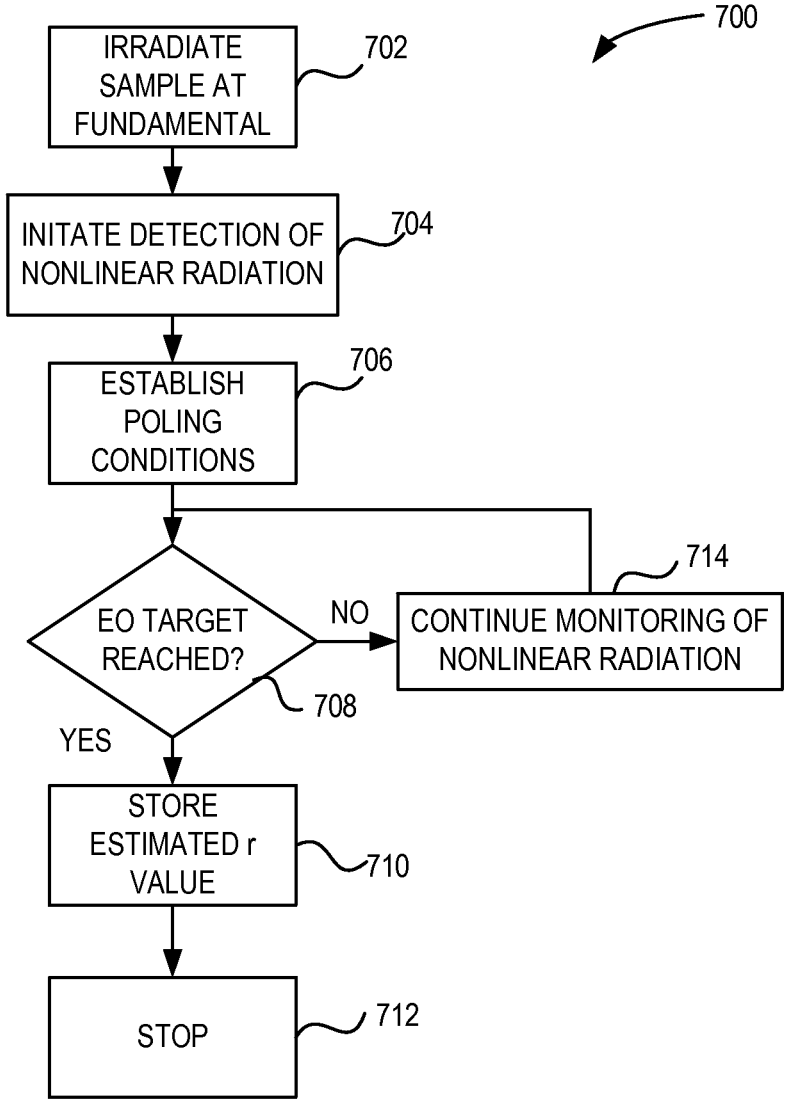
FIG. 7 is a block diagram of a representative method of processing a polymer waveguide device.

With reference to FIG. 7, a method of waveguide device processing includes irradiating a sample at a fundamental wavelength (or a combination of fundamental wavelengths) at 702, and initiating detection of optical radiation resulting from nonlinear processes at 704. At 706, poling conditions in a waveguide polymer are established. In some cases, a waveguide polymer defines a waveguide core while in other examples, a waveguide polymer defines a waveguide cladding. At 708, the extent of poling is evaluated, typically based on an estimated value of one or more electrooptic coefficients or a ratio of such coefficients. If a desired electrooptic target value has been reached, an estimated r value is store at 710, and processing is halted at 712. Otherwise, poling conditions are maintained at 714 until the target is reached. In some alternatives, processing can be halted for other reasons such as failure of an estimated r-value to approach a target value at a suitable rate, or identification of other deficiency in the substrate.

Poling values are generally associated with polymer temperatures and applied electric fields. Electric fields can be applied using a plasma discharge, using coplanar electrodes, or otherwise applied. Polymer temperature can be set using a thermal stage, an oven, or other approaches.

Example 5

Sum and Difference Frequency-Based Measurements

Figure 8:
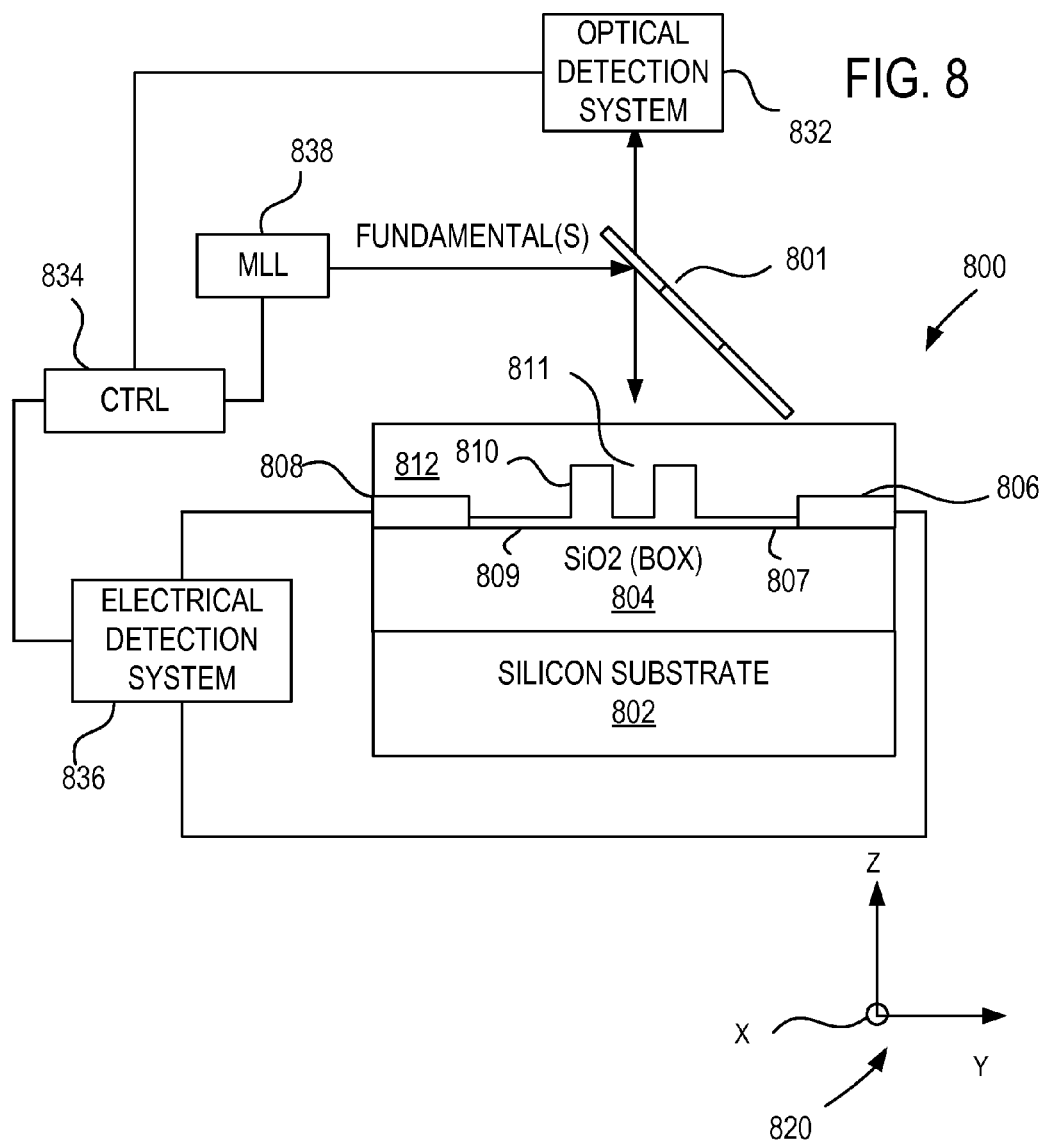
FIG. 8 illustrates a representative silicon slot waveguide having an electrooptic polymer cladding and exposed to a focused optical beam at one or more fundamental wavelengths so as to produce sum and/or difference frequencies at optical frequencies as well as an electrical signal associated with optical rectification.

A representative configuration for sum frequency and/or difference frequency (including optical rectification) based assessment of a slot waveguide 800 is illustrated in FIG. 8. An incident optical beam at one or more fundamental wavelengths is directed to a dichroic beam-splitter 801 that reflects the fundamental beams to a silicon ridge 810 that defines a slot 811. A polymer 812 is arranged to at least partially cover the silicon ridge 810 and/or partially fill the slot 811. The polymer 812 is generally selected so as to be suitable for poling. Metallic electrodes 806, 808 are electrically coupled to silicon layer contacts 807, 809 respectively, so as to establish an electric field in a region around the silicon ridge. In the example of FIG. 8, the polymer layer 812 is arranged as a cladding layer and the silicon ridge 810 as a core layer. A propagation axis in the silicon ridge 810 is parallel to an x-axis of a coordinate system 820. Harmonic optical power generated in response to the incident optical beam is received by the beam-splitter 801 and directed to an optical detection system 832. Harmonic power can be received directly as generated in the polymer or other layers, and as reflected from a silicon/$SiO_x$ or other interface. An electrical detection system 836 is coupled to the electrodes 806, 808 and is responsive to lower frequency electrical signals associated with optical downconversion to electrical frequencies. For example, electrical signals associated with optical rectification can be coupled to the detection system 836. Such electrical signals are generally at frequencies of less than 100 GHz, 10 GHz, or 1 GHz. A control system 834 is coupled to the optical detection system 832 and the electrical detection system 836 so that one or more linear electrooptic coefficients, nonlinear coefficients, or ratios of such coefficients can be obtained as a function of position.

Poling of the polymer layer 812 can be performed by applying a suitable voltage to the electrodes 806, 808 or a poling field can be otherwise provided, and nonlinear power associated with upconversion, downconversion, and/or optical rectification can be used to assess poling extent or otherwise characterize a device for use or processing.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. An apparatus, comprising:
a substrate stage configured to retain a waveguide defined by a polable polymer layer on a substrate;
a beam scanner configured to scan a focused optical beam along an axis of the waveguide, wherein the focused optical beam is at a fundamental wavelength;
an optical detection system configured to detect nonlinear optical radiation from the waveguide at an optical harmonic wavelength responsive to the focused optical beam; and a processing system configured to produce an image of at least a portion of the waveguide based on the scanning of the focused optical beam and the detected optical harmonic radiation and adjust poling conditions based on the detected optical harmonic radiation, wherein the poling conditions include at least one of a polymer temperature or a poling electric field applied to the polymer layer.

2. The apparatus of claim 1, wherein the polable polymer layer is a waveguide cladding layer.

3. The apparatus of claim 1, wherein the polable polymer layer is a waveguide core layer.

4. The apparatus of claim 1, wherein the substrate stage and the beam scanner are configured to scan the focused optical beam along the axis of the waveguide and along an axis parallel to a substrate surface and angled with respect to the waveguide axis.

5. The apparatus of claim 1, wherein the detected optical harmonic radiation is a second harmonic of the focused optical beam and is associated with a poled portion of the polable polymer layer of the waveguide.

6. The apparatus of claim 1, wherein the detected optical harmonic radiation is a third harmonic of the focused optical beam and is associated with waveguide conductor layers.

7. The apparatus of claim 6, wherein the detected optical harmonic radiation is associated with the waveguide conductor layers having a polymer layer covering.

8. The apparatus of claim 1, further comprising a voltage source configured to apply the poling electric field, wherein the processor is configured to assess a poling extent based on the detected optical harmonic radiation.

9. The apparatus of claim 8, wherein the image is associated with electrooptic coefficient values based on the detected optical harmonic radiation.

10. The apparatus of claim 9, wherein the electrooptic coefficient values correspond to values of $r_{33}$ or $r_{13}$ or a ratio thereof.

11. The apparatus of claim 1, wherein the scanned, focused optical beam has a state of polarization selected so that the detected harmonic optical radiation is associated with a selected electrooptic coefficient.

12. A method, comprising:
directing a focused optical beam to a waveguide device retained on a substrate stage, wherein a waveguide of the waveguide device is defined by a polable polymer layer on a substrate;
with a beam scanner, scanning the focused optical beam in a direction parallel to an axis of propagation in the waveguide device, wherein the focused optical beam is at a fundamental wavelength;
detecting optical harmonic radiation at an optical harmonic wavelength produced responsive to the focused optical beam by the waveguide device and producing an image of at least a portion of the waveguide based on the scanning of the focused optical beam and the detected optical harmonic radiation; and
adjusting poling conditions based on the detected optical harmonic radiation, wherein the poling conditions include at least one of polymer temperature or an electric field applied to the polymer layer.

13. The method of claim 12, further comprising producing an estimate of an electrooptic coefficient or a ratio of electrooptic coefficients based on the detected optical harmonic radiation.

14. The method of claim 13, wherein the waveguide device includes a polable polymer layer, and further comprising establishing the poling conditions in at least a portion of the polable polymer layer, wherein the optical harmonic radiation is detected under established poling conditions.

15. The method of claim 14, wherein the poling conditions include an electric field applied with waveguide electrodes.

16. The method of claim 14, further comprising terminating the poling conditions based on the detected optical harmonic radiation.

17. The method of claim 12, wherein the optical harmonic radiation is second harmonic radiation.

18. The method of claim 12, wherein the optical harmonic radiation is third harmonic radiation.

* * * * *